(12) United States Patent
Wenz

(10) Patent No.: US 7,754,005 B2
(45) Date of Patent: Jul. 13, 2010

(54) BONE CEMENT COMPOSITIONS COMPRISING AN INDICATOR AGENT AND RELATED METHODS THEREOF

(75) Inventor: Robert Wenz, Wollstadt (DE)

(73) Assignee: Kyphon Sarl (CH)

( * ) Notice: Subject to any disclaimer, the term of this patent is extended or adjusted under 35 U.S.C. 154(b) by 149 days.

(21) Appl. No.: 11/416,093

(22) Filed: May 2, 2006

(65) Prior Publication Data

US 2007/0260325 A1 Nov. 8, 2007

(51) Int. Cl.
A61L 24/00 (2006.01)
A61L 24/04 (2006.01)

(52) U.S. Cl. ............... 106/690; 106/691; 623/23.62; 523/116; 523/117; 523/115; 523/114

(58) Field of Classification Search ............... 623/23.62; 106/690, 691; 523/116, 117, 115, 114
See application file for complete search history.

(56) References Cited

U.S. PATENT DOCUMENTS

| | | | |
|---|---|---|---|
| 3,746,680 A | 7/1973 | Boricheski | |
| 3,882,858 A * | 5/1975 | Klemm | 606/76 |
| 4,141,864 A | 2/1979 | Rijke et al. | |
| 4,192,021 A | 3/1980 | Deibig et al. | |
| 4,239,113 A * | 12/1980 | Gross et al. | 206/568 |
| 4,341,691 A | 7/1982 | Anuta | |
| 4,404,327 A | 9/1983 | Crugnola et al. | |
| 4,518,430 A | 5/1985 | Brown et al. | |
| 4,588,583 A | 5/1986 | Pietsch et al. | |
| 4,612,053 A | 9/1986 | Brown et al. | |
| 4,629,464 A | 12/1986 | Takata et al. | |
| 4,678,436 A * | 7/1987 | Kondo et al. | 433/228.1 |
| 4,722,948 A | 2/1988 | Sanderson | |
| 4,791,150 A | 12/1988 | Braden et al. | |
| 4,837,279 A * | 6/1989 | Arroyo | 525/193 |
| 4,872,936 A | 10/1989 | Engelbrecht | |
| 4,902,649 A | 2/1990 | Kimura et al. | |
| 4,940,689 A | 7/1990 | Ito | |
| 4,957,352 A | 9/1990 | Yasuda et al. | |
| 4,959,104 A | 9/1990 | Iino et al. | |
| 5,004,501 A | 4/1991 | Faccioli et al. | |
| 5,108,956 A | 4/1992 | Inoue et al. | |
| 5,149,368 A | 9/1992 | Liu et al. | |
| 5,160,371 A | 11/1992 | Ito | |
| 5,171,720 A | 12/1992 | Kawakami | |
| 5,179,065 A | 1/1993 | Ito | |
| 5,204,382 A | 4/1993 | Wallace et al. | |
| 5,205,928 A | 4/1993 | Inoue et al. | |
| 5,226,877 A | 7/1993 | Epstein | |
| 5,262,166 A | 11/1993 | Liu et al. | |
| 5,276,070 A | 1/1994 | Arroyo | |
| 5,281,265 A | 1/1994 | Liu | |
| 5,352,715 A | 10/1994 | Wallace et al. | |
| 5,462,356 A | 10/1995 | Murray | |
| 5,462,722 A | 10/1995 | Liu et al. | |
| 5,522,893 A | 6/1996 | Chow et al. | |
| 5,545,254 A | 8/1996 | Chow et al. | |
| 5,605,713 A | 2/1997 | Boltong | |
| 5,650,108 A | 7/1997 | Nies et al. | |
| 5,695,729 A | 12/1997 | Chow et al. | |
| 5,795,922 A | 8/1998 | Demian et al. | |
| 5,797,873 A | 8/1998 | Franz et al. | |
| 5,814,683 A * | 9/1998 | Branham | 523/161 |
| 5,847,046 A | 12/1998 | Jiang et al. | |
| 5,914,356 A | 6/1999 | Erbe | |
| 5,952,010 A | 9/1999 | Constantz | |
| 6,002,065 A | 12/1999 | Constantz et al. | |
| 6,075,067 A | 6/2000 | Lidgren | |
| 6,124,373 A | 9/2000 | Peter et al. | |
| 6,153,664 A | 11/2000 | Wise et al. | |
| 6,187,046 B1 | 2/2001 | Yamamoto et al. | |
| 6,203,574 B1 | 3/2001 | Kawamura | |
| 6,206,957 B1 | 3/2001 | Driessens et al. | |
| 6,224,635 B1 | 5/2001 | Ricci et al. | |
| 6,231,615 B1 | 5/2001 | Preissman | |
| 6,241,734 B1 | 6/2001 | Scribner et al. | |
| 6,248,110 B1 | 6/2001 | Reiley et al. | |
| 6,273,916 B1 | 8/2001 | Murphy | |
| 6,309,420 B1 | 10/2001 | Preissman | |

(Continued)

FOREIGN PATENT DOCUMENTS

DE 29607832 * 10/1996

(Continued)

OTHER PUBLICATIONS

Translation for WO 03/086327.*

(Continued)

Primary Examiner—C. Melissa Koslow

(57) ABSTRACT

The invention relates to methods, compositions, kits and systems for determining one or more cement material properties. In one variation, a color change agent is introduced into bone cement to allow a physician to determine when a cement has the desired viscosity for insertion into a patient. In another variation, the composition comprises one or more curable bioactive agents and one or more color change agents. The curable bioactive agent(s) may be one or more bone cement (s). These Bone cements contain a color change agent that allows a physician to tell when the cement has reached the property viscosity for insertion of the bone cement into a patient at the bone site.

12 Claims, 1 Drawing Sheet

U.S. PATENT DOCUMENTS

| | | | |
|---|---|---|---|
| 6,325,992 | B1 | 12/2001 | Chow et al. |
| 6,338,810 | B1 | 1/2002 | Carpena et al. |
| 6,436,143 | B1 | 8/2002 | Ross et al. |
| 6,497,901 | B1 | 12/2002 | Royer |
| 6,521,264 | B1 | 2/2003 | Lacout et al. |
| 6,547,866 | B1 | 4/2003 | Edwards et al. |
| 6,562,755 | B1 | 5/2003 | Halbrook, Jr. et al. |
| 6,593,394 | B1 | 7/2003 | Li et al. |
| 6,613,054 | B2 | 9/2003 | Scribner et al. |
| 6,692,563 | B2 | 2/2004 | Zimmermann |
| 6,908,506 | B2 | 6/2005 | Zimmermann |
| 6,953,594 | B2 | 10/2005 | Lee et al. |
| 6,994,726 | B2 | 2/2006 | Lin et al. |
| 7,008,433 | B2 | 3/2006 | Voellmicke et al. |
| 7,115,163 | B2 | 10/2006 | Zimmermann |
| 7,135,027 | B2 | 11/2006 | Delmotte |
| 7,138,442 | B2 | 11/2006 | Smith et al. |
| 7,160,932 | B2 | 1/2007 | Schilke et al. |
| 7,273,523 | B2 | 9/2007 | Wenz |
| 7,569,621 | B2 * | 8/2009 | Kuhn et al. ............. 523/115 |
| 2001/0012968 | A1 | 8/2001 | Preissman |
| 2002/0152929 | A1 * | 10/2002 | Burgath et al. ............ 106/35 |
| 2002/0167480 | A1 | 11/2002 | Johnson et al. |
| 2002/0187104 | A1 | 12/2002 | Li et al. |
| 2002/0191487 | A1 | 12/2002 | Sand |
| 2003/0031698 | A1 | 2/2003 | Roeder et al. |
| 2003/0032964 | A1 | 2/2003 | Watkins et al. |
| 2003/0055512 | A1 | 3/2003 | Genin et al. |
| 2003/0139488 | A1 | 7/2003 | Wojciak |
| 2003/0161858 | A1 | 8/2003 | Lidgren |
| 2003/0180344 | A1 | 9/2003 | Wise et al. |
| 2004/0048947 | A1 | 3/2004 | Lidgren et al. |
| 2004/0122359 | A1 | 6/2004 | Wenz et al. |
| 2004/0157952 | A1 | 8/2004 | Soffiati et al. |
| 2004/0226479 | A1 | 11/2004 | Lyles et al. |
| 2004/0265385 | A1 | 12/2004 | West |
| 2005/0105384 | A1 | 5/2005 | Eder et al. |
| 2005/0142211 | A1 | 6/2005 | Wenz |
| 2005/0199156 | A1 | 9/2005 | Khairoun et al. |
| 2005/0246036 | A1 | 11/2005 | Zimmermann |
| 2005/0256220 | A1 | 11/2005 | Lavergne et al. |
| 2006/0079905 | A1 | 4/2006 | Beyar et al. |
| 2007/0021526 | A1 * | 1/2007 | He et al. ............... 523/116 |
| 2007/0032567 | A1 | 2/2007 | Beyar et al. |
| 2007/0048382 | A1 | 3/2007 | Meyer et al. |
| 2007/0128245 | A1 | 6/2007 | Rosenberg et al. |
| 2007/0191964 | A1 | 8/2007 | Preissman |
| 2007/0254011 | A1 | 11/2007 | Schnabelrauch et al. |

FOREIGN PATENT DOCUMENTS

| | | |
|---|---|---|
| DE | 20218668 | 3/2003 |
| DE | 20218668 U1 | 3/2003 |
| EP | 0473048 A2 | 3/1992 |
| EP | 0511868 A2 | 11/1992 |
| EP | 0520690 A2 | 12/1992 |
| EP | 0543765 A1 | 5/1993 |
| EP | 1002513 A1 | 5/2000 |
| EP | 125576 B | 8/2003 |
| EP | 0835668 B1 | 11/2007 |
| JP | 01320251 | 12/1989 |
| JP | 02116684 | 5/1990 |
| WO | WO9202478 A1 | 2/1992 |
| WO | WO9513835 A1 | 5/1995 |
| WO | WO9614265 A1 | 5/1996 |
| WO | WO0149327 A2 | 7/2001 |
| WO | WO0232827 A1 | 4/2002 |
| WO | 0236527 A | 5/2002 |
| WO | WO0236518 A1 | 5/2002 |
| WO | WO 03/086327 * | 10/2003 |
| WO | WO03086327 A2 | 10/2003 |
| WO | WO03103734 A1 | 12/2003 |
| WO | WO2004050131 A1 | 6/2004 |
| WO | WO2005009481 A2 | 2/2005 |
| WO | WO2007025633 A2 | 3/2007 |
| WO | WO2007067561 A2 | 6/2007 |

OTHER PUBLICATIONS

Ishikawa et al., "Effects of neutral sodium hydrogen phosphate on setting reaction and mechanical strength of hydroxyapatite putty," J Biomed Mater Res, 44, 322-329, 1999.

Abdullah et al., Biodegradable Polymeric Bone Cement Formed from Hydroxyapatite, Poly (Propylene Fumerate), Poly (Vinyl Pyrrolidone) and Benzoyl Peroxide, Materials Science and Technology, vol. 20, No. 9, pp. 1084-1086 (2004) (abstract only).

Baroud et al., Influence of Oscillatory Mixing on the Injectability of Three Acrylic and Two Calcium-Phosphate Bone Cements for Vertebroplasty, J Biomed Mater Res, vol. 68B, No. 1, pp. 105-111 (2004) (abstract only).

Beruto et al., Use of Alpha-Tricalcium Phosphate (TCP) as Powders and as an Aqueous Dispersion to Modify Processing, Microstructure, and Mechanical Properties of Polymethylmethacrylate (PMMA) Bone Cements and to Produce Bone-Substitute Compounds, J Biomed Mater Res, vol. 49, No. 4, pp. 498-505 (2000) (abstract only).

Bezzi G. et al., A novel sol-gel technique for hydroxyapatite preparation, Materials Chemistry and Physics, 2003, 78:816-824, entire document.

Bonfield et al., Hydroxyapatite Composite Biomaterials—Evolution and Applications, Materials World, vol. 5, No. 1, pp. 18-20 (1997).

Brown, et al., A new calcium phosphate, water-setting cement, Cements Research Progress 1986 pp. 352-379 (1987).

Canul-Chuil et al., Comparative Study of Bone Cements prepared with either HA or alpha-TCP and Functionalized Methacrylates, J Biomed Mater Res, vol. 64B. No. 1, pp. 27-37 (2003) (abstract only).

Chu et al., Hydroxyapatite/PMMA Composites as Bone Cements, Biomed Mater Eng, vol. 14, No. 1, pp. 87-105 (2004) (abstract only).

Dalby et al., Initial Interaction of Osteoblasts with the Surface of a Hydroxyapatite-Poly (Methylmethacrylate) Cement, Biomaterials, vol. 22, No. 13, pp. 1739-1747 (2001) (abstract only).

Eule et al., Bioactive Bone Cement: The Solution for Osteolysis and Late Implant Loosening, SRS Annual Meeting: Scientific Program Abstracts, pp. 98 (2002).

Frankenburg et al., Evaluation of Hydroxyapatite/Bis-GMA Bone Cement for Fixation of Cemented Hip Stems, The Third Combined Meeting of the Orthopaedic Research Societies of the USA, Canada, Europe and Japan, Hamamatsu City, Japan (1998).

Grigorian et al., Evolution of Tissue Structures in the Mandible after Implantation of Plate from Polymrthylmethacrylate and its Compositions with Hydroxyapatite, Stomatolgiia, vol. 82, No. 2, pp. 10-14 (2003) (abstract only).

Heness et al., Biocomposites—Bone Cement, Hydroxyapatite and Biomimetic Composites for Bone Repair, Innovative Bioceramics, Materials Forum, vol. 27 (2004) (3 page abstract).

Hitchon et al., Comparison of the Biomechanics of Hydroxyapatite and Polymethylmethacrylate Vertebroplasty in a Cadaveric Spinal Compression Fracture Model, J. Neurosurg, vol. 95, Suppl. 2, pp. 215-220, (2001) (abstract only).

Jager et al., Comprehensive Biocompatibility Testing of a New PMMA-hA Bone Cement Versus Conventional PMMA Cement in Vitro, J. Biomater Sci Polym Ed, vol. 14, No. 11, pp. 1283-1298 (2003) (abstract only).

Lee C L et al., Laser Ablation of Dyed Acrylic Bone Cement, Lasers in Surgery and Medicine, Wiley-Liss, New York, US vol. 20, 3, Jan. 1, 1997, pp. 280-289, XP000694435, ISSN:0196-8092.

Lee R.R. et al, Interactions between bone and hydroxyapatite filled 4 META/MMA-TBB adhesive cement in vitro and in physiological environment, 1996, IEEE Xplore, pp. 18-21, entire document.

Li et al., A Novel Injectable Bioactive Bone Cement for Spinal Surgery: A Developmental and Preclinical Study, J Biomed Mater Res, vol. 52, No. 1,,pp.164-170 (2000) (abstract only).

Liu et al., Influence of the Aspect Ratio of Bioactive Nanofillers on Rheological Behavior of PMMA-Based Orthopedic Materials, J Biomed Mater Res, vol. 71B, No. 1, pp. 116-122 (2004) (abstract only).

Liao et al., A Fundamental Study on Bioreactions of Sr-HA, Hua Xi Kou Qiang Yi Xue Za Zhi, vol. 20, No. 3, pp. 172-174 183 (2002) (abstract only).

Miyazaki et al., Bioactive PMMA Bone Cement Prepared by Modification with Methacryloxpropyltrimethoxysilane and Calcium Chloride, J Biomed Mater Res, vol. 67A, No. 4, pp. 1417-1423 (2003) (abstract only).

Mousa et al., Biological and Mechanical Properties of PMMA-Based Bioactive Bone Cements, Biomaterials, vol. 21, No. 21, pp. 2137-2146 (2000) (abstract only).

Okada et al., Transmission Electron Microscopic Study of Interface Between Bioactive Bone Cement and Bone: Comparison of Apatite and Wollastonite Containing Glass-Ceramic Filler with Hydroxyapatite and Beta-Tricalcium Phosphate Filler, J Biomed Mater Res, vol. 45, No. 4, pp. 277-284 (1999) (abstract only).

Oonishi et al., Hydroxyapatite Granules Interposed at Bone-Cement Interface in Total Hip Replacements: Histological Study of Retrieved Specimens, J Biomed Mater Res, vol. 53, No. 2, pp. 174-180 (2000) (abstract only).

Patel et al., Comparison of Sintering and Mechanical Properties of Hydroxyapatite and Silicon-Substituted Hydroxyapatite, Key Engineering Materials, 240-242, 919-22 (2003) (abstract only).

Patent Abstract XP-002180738 (1 page total), Park et al., "Compositional effects of CaO-SiO2-P2O5 bioactive cement on hardening and hydroxyapatite formation" Yoop Hakhoechi, 31(5):502-512 (1994).

Patent Abstract XP-002180739 (1 page total), Nippon Electric Glass Co., "Bone-repair material for fast, strong bonding—contains glass and/or crystalline glass powder, a.q. phosphate solution and bond formation promoter" (1992).

The term "PRE-", Merriam-Webster Online Dictionary, at the web: http://www.m-w.com, p. 1-2.

Serbetci et al., Mechanical and Thermal Properties of Hydroxyapatite-Impregnated Bone Cement, Turk J Med Sci, vol. 30, pp. 543-549 (2000) (abstract only).

Turner et al., Hydroxyapatite Composite Resin Cement Augmentation of Pedicle Screw Fixation, Clinical Orthopaedics & Related Research, vol. 1, No. 406, pp. 253-261 (2003) (abstract only).

Wong et al., In Vivo Cancellous Bone Remodeling on a Strontium-Containing Hydroxyapatite (sr-HA) Bioactive Cement, J Biomed Mater Res A, vol. 68, No. 3, pp. 513-521 (2004) (abstract only).).

Wong et al., Ultrastructural Study of Mineralization of a Strontium-Containing Hydroxyapatite (Sr-HA) Cement in Vivio, J Biomed Mater Res A, vol. 70, No. 3, pp. 428-435 (2004) (abstract only.

Zhao et al., Surface Treatment of Injectable Strontium-Containing Bioactive Bone Cement for Vertebroplasty, J. Biomed Mater Res B Appl Biomater, vol. 69, No.1, pp. 79-86 (2004) (abstract only).

International Search Report and Written Opinion, International Application No. PCT/US2007/012723, mailed Dec. 3, 2008.

International Search Report and Written Opinion, International Application No. PCT/US2007/008789, mailed Nov. 13, 2008.

International Search Report and Written Opinion, International Application No. PCT/EP2006/007750, mailed Jun. 11, 2007.

International Search Report, International Application No. PCT/US03/38580, mailed May 19, 2004.

International Search Report, International Application No. PCT/US2005/014616, mailed Sep. 12, 2005.

Heini, P.F., et al., "Bone substitutes in vertebroplasty," *Eur. Spine J.*, Jun. 14, 2001, vol. 10, pp. S205-S213.

Li, Y., et al. "Preparation of amorphous calcium phosphate in the presence of poly(ethylene glycol)," *Journal of Materials Science Letters*, 2003, vol. 22, pp. 1015-1016.

International Search Report, WIPO, International Application No. PCT/US2007/012723, Jan. 22, 2009, International Publication No. WO2007/145824 A3, publication date Dec. 21, 2007.

Harper, et al., Tensile Characteristics of Ten Commercial Acrylic Bone Cements, J. Biomed Mater Res: Appl Biomater., vol. 53, pp. 605-616 (2000).

* cited by examiner

SCHEME 1

BONE CEMENT COMPOSITIONS COMPRISING AN INDICATOR AGENT AND RELATED METHODS THEREOF

BACKGROUND OF THE INVENTION

In various medical applications, it is desirable to prepare bone cements with a specific range or threshold level of viscosity for placement into a cavity within a patient—s bone. Bone cements that are viscous may be particularly suitable for delivery through a plunger system. In certain medical applications, cement delivered in a low viscosity state may cause medical complications. For example, if the viscosity is not sufficiently viscous, the bone cement may leak outside of the bone cavity, potentially leading to contact of external tissue, such as nerve contact, which may cause nerve damage resulting in subsequent paralysis of the patient. If the viscosity is too viscous, the bone cement may not completely fill all of the voids in the bone cavity prior to the cement hardening, leading to incomplete filling and a bone that is weaker and more susceptible to damage (e.g., fractures).

Previously, physicians would determine a correct viscosity by feel, i.e., rubbing the cement between their fingers to make a judgment on whether the cement is the correct viscosity for loading the cement into a plunger for insertion into a patient. However, judging the cement by feel can be imprecise and may lead to the problems discussed above if the viscosity is not correct. Therefore, an improved approach for determining cement viscosity may be desirable.

BRIEF SUMMARY OF THE INVENTION

The invention relates to methods, compositions, kits and systems for determining one or more cement material properties (e.g., viscosity). In one variation, a color change agent is introduced into a bone cement to allow a physician to determine when the cement has reached the desired viscosity for insertion into a patient.

BRIEF DESCRIPTION OF THE DRAWINGS

The present disclosure may be better understood, and its numerous features and advantages made apparent to those skilled in the art by referencing the accompanying drawings.

DETAILED DESCRIPTION OF THE INVENTION

Figure 1:
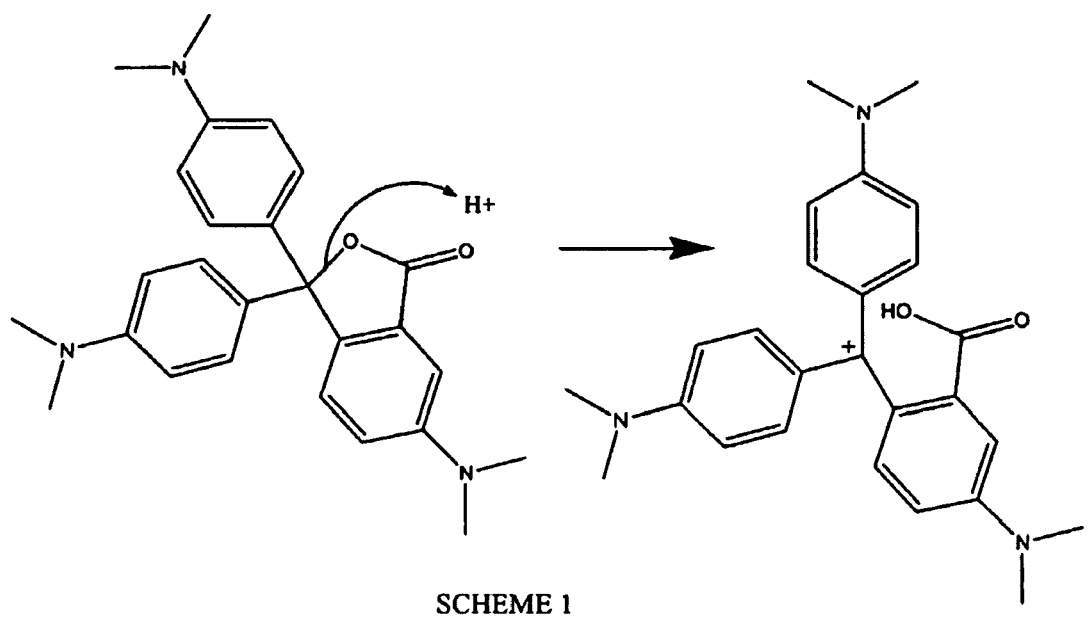
FIG. 1 includes an illustration of an exemplary thermosensitive dye.

In one variation of the invention, a color change agent is incorporated into a bone cement to allow a physician to tell when a cement has the desired viscosity for insertion into a patient. It should be understood that a patient refers to any animal that could logically use bone cement including but not limited to humans, other primates, domestics pets, livestock, wild game, and any other animal that has bones. Moreover, in the instant invention, when a physician is referenced, it should be understood that it could just as easily refer to a veterinarian or a clinician or any other person who may make use of the bone cement formulations of the present invention.

Application time can be crucial for delivery of bone cement into bones such as vertebral bodies, since the appropriate viscosity can prevent leakages when performing bone filling surgical procedures such as Kyphoplasty or Vertebroplasty. The determination of the right viscosity of a bone cement polymer during its hardening process may also be important to determine the right time for the insertion of knee, hip, elbow and other prostheses. Traditionally, a surgeon determined the optimal viscosity of the polymerizing mass by extruding the material out of a loaded bone filler device (BFD) (for example, during Kyphoplasty) after several given time intervals in order to choose the desired viscosity or dough state for application of the bone cement.

In one embodiment of the present invention, the use of an thermosensitve dye allows the determination of the viscosity of the material by visualizing a color change, so that a physician or surgeon can empty his/her cement delivery device (e.g. a bone cement delivery cannula, etc.) and apply the bone cement when the color of the bone cement begins to change. This makes the procedure both more comfortable for the surgeon as the surgeon does not have to test viscosity in his/her hand as well as significantly safer for the patient because the cement is applied at the appropriate time.

In an embodiment, the thermosensitive dye can be added to either a bone cement powder or a bone cement liquid. The bone cement powder and the bone cement liquid are then mixed. The mixing of the bone cement powder and the bone cement liquid leads to a chemical reaction that triggers a color change agent to change colors allowing a surgeon to determine the correct time for application of the paste.

In another embodiment, the color change agent is visibly discernible to a user. Without being bound by theory, it is believed that upon first mixing the liquid and the powder elements together, there can be highly localized chemical reactions that are occurring. Thus, one may see small color changes occurring in defined portions of the dry and wet components of the cement prior to mixing. These color changes may be observable on a pantone scale, but may not be readily apparent to the human eye. With a uniform mixing of the cement, these localized reactions may be lessened depending on the relative concentrations of the color change agent and consequently, based on the order of kinetics (e.g., pseudo first order, second order or higher order kinetics). Moreover, as the cement becomes more viscous, there is also a change in color and this change may be from grayish to less grayish and therefore not readily apparent to the naked eye. However, the presence of a color change agent will likely lead to a "visibly discernible" color change (where "visibly discernible" is a color change that is apparent to the naked eye of a person with normal color vision).

A plurality of possible materials can be used as bone cements. For example, bone cements that generate an exothermic reaction such as polymethyl methacrylate (PMMA) bone cements may be particularly suitable cements for use with a thermosensitive indicator agent. PMMA bone cement has been used in orthopedic surgery for over 40 years and is known to have a relatively large exotherm. Other cements are suitable for the present invention as long as a color change agent is added to the cement and the color change agent undergoes a color change with a change in a material (e.g. physical and/or chemical) property of the cement, such as a change in temperature, pH, concentration of a component (like a starting material that is being converted to another material), or some other physical property. As one of ordinary skill in the art having the benefit of this disclosure would appreciate, an indicator agent for detecting such physical/chemical property changes can be used to indicate the particular material state of the cement.

Typically, PMMA bone cements are provided to the physician as two-phase materials that consist of a liquid methylmethacrylate monomer and a fine pre-polymerized polymethylmethacrylate powder. The components are usually packaged separately, and may optionally be mixed together in the operating room in a vacuum-mixing chamber (or alternatively, may be mixed without using a vacuum-mixing chamber) and inserted under pressure (or optionally may be inserted without pressure) into the prepared bone cavity before the polymerization reaction is complete. The liquid monomer may contain the promoter or accelerator (to initiate the free-radical reaction to generate PMMA) and a stabilizer (to prolong shelf-life) and the powder may contain an initiator (a catalyst) and a radiopacifier. Radiopaque material is commonly added to bone cement to enable the radiologist to "see" the cement mantle, monitor its integrity and observe the presence of defects.

A bone cement may be made as described in, for example, U.S. Pat. No. 6,593,394, which is herein incorporated by reference in its entirety for all purposes. As long as there is a physical and or chemical property change in the cement such as a change in temperature or pH, a color change agent (such as a thermosensitive dye) can undergo a color change that can be detected. The color change can be correlated with another physical change such as a change in viscosity that indicates that a cement has obtained the desired viscosity that is ready to insert into a bone.

A "color change agent" as referred to in the instant invention refers to an agent that is added to a composition for the purpose of changing color when a physical and/or chemical property of the composition changes. A "color change agent" should be distinguished from components in a composition that are not added for the purpose of changing color even if the composition may change color upon a physical change. In this regard, it is noted that sometimes a bone cement that does not have a "color change agent" added to it may as a result of the bone cement undergoing a physical change (such as, for example, a change in viscosity) undergo a slight color change. The component(s) that cause this color change are not "color change agents" unless they are added for the express purpose of undergoing the color change to serve as a visual indicator. The color change agent may be configured to cause the cement to reach a specific spectrum/color target when the property of the cement has reached a pre-defined threshold. In one variation, the color agent and cement composition may be configured to achieve a specific color target/threshold when a specific viscosity is reached. For example, one may pre-calibrate a particular cement composition to determine the correlation between the exothermic reaction and the cement viscosity. Base on this calibration a thermo sensitive dye may be incorporate into the cement to induce a color change at specific range or exothermic activity such as to indicate a specific viscosity has been reached. In another example, the cement and color change agent composition is pre-calibrated to determine a color reference chart that indicates the correlation between cement viscosity and the color of the cement. The color reference chart may be provided with the cement ingredient in an package or kit to allow the physician to monitor the cement viscosity through visual feedback. The cement ingredient materials along with an indicator agent (e.g., color change agent) may be packaged with a cement mixer.

It should be understood that the "color change agent" of the present invention will undergo a color change after a desired change in a physical and/or chemical property and this color change can be detected by an instrument (or by the human eye). If the color change is detected by an instrument, the color change can be detected either at a monochromatic wavelength or at polychromatic wavelengths by using spectroscopic techniques that are known to those of ordinary skill in the art, such as, for example, absorption or emission spectroscopy at a given wavelength.

In an embodiment, the bone cement according to the present invention may be supplied in a powder-liquid phase (comprising a powder phase and a liquid phase). In this powder-liquid phase, the powder phase material may include surface-treated Sr—HA powder and fumed silica, and a polymerization initiator, whereas the liquid phase may include resins and a polymerization accelerator. Either or both the powder and liquid phase may contain the color change agent, such as a thermosensitive dye. The surgeon or physician mixes the powder phase material with the liquid phase material, which starts the polymerization process. Because the polymerization process undergoes a physical change (such as a change in temperature), the color change agent (such as a thermosensitive dye) will undergo a chemical change leading to a change in chemical structure and a corresponding change in light absorption (i.e., color).

With respect to the color change, it should be understood that the color change is occurring over time. Although the color may change relatively rapidly (depending on the kinetics), the cement may not be ready at the first appearance of a color (or disappearance thereof), but rather when the overall composition has a substantially that colors tint (or substantially when the color disappears).

In an embodiment of the invention, thermochromic dyes (dyes that change color due to a change in temperature) are used. Thermochromic dyes may be based on mixtures of leucodyes with suitable other chemicals, which display a color change (usually between a colorless leuco form and the colored form of the dye) dependent on the temperature. The dyes can be applied on the bone cement directly.

Alternatively, the dyes can be in the form of microcapsules with a mixture sealed inside. An illustrative example is a microcapsule that contains crystal violet lactone, a weak acid, and a dissociable salt dissolved in a nonpolar or slightly polar solvent liquid crystal solvent such as dodecanol or another suitable liquid crystal solvent. When the mixture is a solid, the dye exists in its lactone leuco form. However, when the liquid crystal solvent melts, the salt dissociates, the pH inside the microcapsule lowers (making protons readily available), the dye becomes protonated, and the lactone ring opens causing its absorption spectrum to shift, absorbing in the visible spectrum, such as a deeply violet color for crystal violet lactone. Please see the mechanism in Scheme 1 for an example of how a color change may occur in a given compound. In this scheme, the non-planar crystal violet lactone compound is colorless but upon protonation of the lactone ring, the lactone ring opens generating a substantially planar conjugated pi system satisfying the Hückel rules of aromaticity resulting in a dye that is highly colored (i.e., a dye that absorbs in the visible part of the spectrum). Those of ordinary skill in the art will recognize that when the lactone ring opens the compound undergoes strain relief, which generates the substantially planar structure leading to a highly conjugated system (and thus a compound that absorbs in the visible range of the electromagnetic spectrum).

Although the temperature change of the dye system shown in scheme 1 is the initiator that causes the crystal violet lactone to undergo a change from colorless to colored, it should be understood that the opposite reaction is contemplated and within the scope of the invention (going from colored to colorless). The reverse reaction or a comparable reaction would lead to a change from a colored product to a product that is not colored. The reaction in scheme 1 might also be considered a halochromic reaction (a color change caused by a change in pH).

Moreover, although the above is described with respect to an exothermic reaction, it should be understood that the above color change may occur in an endothermic reaction wherein a cooling of the mixture results in a change of color (either from colored to colorless or from colorless to colored).

In one embodiment of the invention, spirolactones (as shown in FIG. 1 as Scheme 1) can be used as the thermosensitive dye. It is contemplated and therefore within the scope of the invention that other thermosensitive dyes can be used, such as fluorans, spiropyrans, and fulgides. Weak acids that can be used as proton donors include bisphenol A, parabens, 1,2,3-triazole derivatives, and 4-hydroxycoumarin. These weak acids are the proton donor that changes the dye molecule between its leuco form and its protonated colored form. Stronger Bronsted acids (better proton donors) can also be used but they tend to make the color change irreversible. Other thermosensitive dyes that can be used include an oxazine-based leuco thermosensitive dye (e.g. "CSB-12" a product of Hodogaya Chemicals Co.), a spiropyran-based leuco thermosensitive dye (e.g. "CSR-13" a product of Hodogaya Chemicals Co.), a quinoline-based thermosensitive dye (e.g. "CSY-13" a product of Hodogaya Chemicals CO and the like.

A plurality of thermosensitive dyes are known and are available commercially. The thermosensitive dyes are not particularly limited, but it is desired that dyes that are not toxic are used. A plurality of thermosensitive dyes are available that change colors at a variety of temperatures. Suitable commercially available thermochromic dyes are known which activate at temperatures in the range of 21 to 51° C. These dyes include 744020TC (thermochromic blue), 744010TC (thermochromic turquoise), 744027TC (thermochromic yellow), 734010TC(thermochromic rose), 724010TC (thermochromic orange), 754027TC (thermochromic green) all sold by SICPA Securink Corp. of Springfield, Va. There are also thermochromic dyes which lose color when heated, i.e., change from a color to clear. These dyes include the compounds 178002TC (Black/clear) from SICPA Securink Corp., which is active at 27 to 36° C. Compounds from SICPA Securink Corp. which are active at 22-31° C. include: 128001TC (orange/clear), 1384175TC (rose/clear), 150015TC (green/clear), 148003TC (blue/clear), 17800TC (black/clear), 14001TCBR (blue/red) and 128001TCY (orange/yellow). Compounds from SICPA Securink Corp. which are active from 24-33° C. include: 118000TC (yellow/clear), 128002TC (orange/clear), 138103TC (vermillion/clear), 15002TC (green/clear), 14001TC (blue/clear), 14000TCBR (blue/red) and 128001TCY (orange/yellow). Compounds from SICPA Securink Corp. which are active at 24 to 33° C. include: 11800TC (yellow/clear), 128002TC (orange/clear), 138103TC (vermillion/clear), 15002TC (green/clear), 14001TC (blue/clear), 14000TCBR (blue/red) and 128002TC (orange/yellow). Compounds from SICPA Securink Corp. which are active at 32 to 41° C. include: 13001TC (rose/clear), 148002TC (blue/clear), 178001TC (black/clear) and 178002TCBR (blue/red). The dye to be used is not particularly limited as long as it undergoes a change in color with a change in a physical property of the bone cement. Moreover, because the bone cement is to be used in a body, it is desired that the color change agent be not particularly toxic. Preferably, the color change agent is biocompatible.

Other color change agents that may be used include indicators that may change color hues with a change in pH, such as a series of indicators that are natural products, such as a natural product from a cabbage. Because the cement is to be used in a patient, it is generally desired that if an indicator is to be used, that it's biological toxicity be limited.

As can be seen from the above description regarding dyes, there are a wide variety of dyes that can be used. These dyes have diverse temperature ranges where a color change occurs. Thus, different dyes can be used depending on the temperature change that occurs in the cement. It should be apparent that any of a plurality of different cement materials can be used as long as the cement undergoes even the slightest exothermic reaction (or endothermic reaction to send the color change the other way) and the dye can be targeted for the temperature range. Bone or tissue necrosis may occur at very elevated temperatures so it may be advisable to avoid highly exothermic reactions when making the bone cements. In this regard, there are a plurality of means of limiting the reaction temperature when making the bone cement, including adding compounds that are known to reduce the temperature, or alternatively, by irrigation with a cool, physiological saline solution or by other means such as reducing the size of cement mantles (for example to 2-4 mm). By carefully monitoring the components and the means of making the cement, the temperature can be carefully controlled and the thermosensitive dye can be chosen accordingly.

In an embodiment, the color change can be detected by visually inspecting the color change. Alternatively, a spectrophotometer or some other optical sensor instrument can be used to detect the color change. Using an optical sensor is advantageous in that a precise time can be determined as to when the cement has obtained the optimal viscosity whereas visually inspecting the color change is advantageous in that it is less expensive as the optical sensor instrument is not needed. Moreover, using an instrument that can detect color change allows one to find the optimal viscosity when tints of various colors are detected (i.e., small changes on the pantone scale). Generally, the color change of the entire mix will determine when the cement has obtained the optimal viscosity for use.

In an embodiment of the present invention, 10 parts of PMMA bone cement can be used with 0.1-2 parts or 0.2-0.4 parts of thermosensitive dye. The bone cement can be made with, any one or more of the following components: PMMA (or alternatively any of a number of co-polymers can be used, such as methyl methacrylate-styrene copolymer, urethane acrylates, PEG-mono/di-acrylates/methacrylates, epoxidresins, bisphenol-A-glycidyldimetharcrylate/triethylene-glycoldimethacrylate formulations), benzoyl peroxide, barium sulfate or zirconium dioxide, N,N-dimethyl toluidine, hydroquinone, ascorbic acid, ethanol, and thermosensitive dye. For example, the bone cement may be made with 80-90% PMMA (or alternatively any of a number of co-polymers can be used, such as methyl methacrylate-styrene copolymer), 1-3% benzoyl peroxide, 8-14% barium sulfate or zirconium dioxide, 0.2-1.0% N,N-dimethyl toluidine, 0.01-0.1% hydroquinone, 0.01-0.1% ascorbic acid, 0.5-1.5% ethanol, and 0.1-0.4% thermosensitive dye and other components such as antibiotics, anticancer agents, and/or re-enforcing materials and the like.

In an exemplary embodiment of the present invention, 10 grams of PMMA bone cement is used with 0.3 grams of a blue thermosensitive dye that is in a packaging material polymer (such as polypropylene, polystyrol, polyethylene terephthalate, and other similar polymers). The PMMA bone cement is made of a liquid component and a powder component. The thermosensitive dye in a packaging material polymer is associated with the powder component. Upon mixing the liquid component and the powder component (containing the thermosensitive dye) an exothermic reaction takes place. The exothermic reaction reaches a temperature at which the thermosensitive dye undergoes a reaction that causes the dye to go from a bluish tint to a less bluish tint to colorless. In this embodiment, the time at which the dye first starts to change color is when the bone cement has the optimal viscosity for applying the bone cement to a bone.

The bone cement can be mixed in a plunger (or syringe) or alternatively, in a reaction flask (and then loaded into a device for applying the bone cement). If the mixing occurs in a plunger (or syringe) it is desirable for the plunger (or syringe) to be transparent so that the changing color is readily observable.

It is contemplated and therefore within the scope of the present invention that the bone cement may contain additional components. These additional components include one or more antibiotics such as gentamicin, gentamicin sulfate, erythromycin, tobramycin, vancomycin, cefazolin, oxacillin, cefotaxime, colistin, clindamycin, and/or fusidic acid. It is desired that the antibiotic or antibiotics that are used are stable or at least somewhat stable under heat conditions or under conditions wherein the antibiotic can tolerate some change in physical conditions such as a change in the pH. This is because the color change in the bone cement occurs because of a change in physical condition. One reason why gentamicin sulfate is a suitable antibiotic for the present invention is because it is wide spectrum antibiotic that is relatively stable at diverse temperatures.

Alternatively, and/or additionally, additional components that can be added to the bone cement of the present invention include one or more radiopacifier compounds such as barium sulfate, 2-[2',3',5'-triiodobenzoyl]ethyl methacrylate (TIBMA), 3,5-diiodine salicylic methacrylate (DISMA), and/or zirconium(IV) oxide. It is contemplated that other compounds that can be seen under fluoroscopic guidance can be used as radiopacifier compounds.

Additionally, anticancer agents can be added to the bone cement such as 6-mercaptopurine, methotrexate and/or cisplatin.

Other components that can be added include re-enforcing materials such as hydroxy apatite (HA) powder, $K_2O$—$Na_2$—$CaO$—$MgO$—$SiO_2$—$P_2O_5$ crystallized glass powder, calcium phosphate, carbon, graphite, aramid, bone particle, polyethylene, titanium, ultra high weight polyethylene, polymethylmethacrylate fibers in a cement matrix, tricalcium phosphate, and hydroxycarbonate apatite, and the like.

Thus, in an embodiment, the present invention is directed to a composition comprising a curable bioactive agent and a color change agent. In an embodiment, the present invention is directed to a composition comprising a bone cement and a color change agent. The color change agent of the present invention in one embodiment is a thermosensitive dye. One or more leucodyes are suitable as thermosensitive dyes that can be used in the present invention. Any change in color from a color to colorless or from colorless to a color is contemplated. An example of a contemplated color change is from blue to colorless or from colorless to blue. Other color changes include whitish/grayish to bluish, whitish to redish, or any color change that has a color change agent available that will change from one color hue to another color hue based on a physical or chemical property changing.

Bone cements that undergo a change in a physical property such as polymethyl methacrylate polymer cements are suitable for the present invention. If a polymethyl methacrylate polymer cement is used, the bone cement generally is comprised of a bone cement powder and a bone cement liquid, which is generally made by mixing together the bone cement powder with the bone cement liquid.

In an embodiment, the bone cement of the present invention further comprises one or members selected from the group of an antibiotic, a radiopacifier compound, an anticancer agent, and a re-enforcing material.

The antibiotic, the radiopacifier compound, the anticancer agent, or the re-enforcing material is selected from one or members from the group consisting of gentamicin sulfate, erythromycin, tobramycin, vancomycin, cefazolin, oxacillin, cefotaxime, colistin, clindamycin, fusidic acid, barium sulfate, zirconium(IV) oxide, methotrexate, cisplatin, carbon, graphite, aramid, bone particle, polyethylene, titanium, ultra high weight polyethylene, polymethylmethacrylate fibers in a cement matrix, tricalcium phosphate, and hydroxycarbonate apatite.

In another embodiment, the present invention relates to a method of preparing a bone cement containing a color change agent wherein the method comprises: mixing together a powder and liquid phase to generate a bone cement, wherein either or both of the powder or liquid phase contain the color change agent.

In an embodiment of this method, the color change agent undergoes a color change activated by either a change in temperature or a change in pH.

In an embodiment of the method, either or both of the powder or the liquid phase contain one or more members selected from the group consisting of gentamicin sulfate, erythromycin, tobramycin, vancomycin, cefazolin, oxacillin, cefotaxime, colistin, clindamycin, fusidic acid, barium sulfate, zirconium(IV) oxide, methotrexate, cisplatin, carbon, graphite, aramid, bone particle, polyethylene, titanium, ultra high weight polyethylene, polymethylmethacrylate fibers in a cement matrix, tricalcium phosphate, and hydroxycarbonate apatite.

In an alternate embodiment, the present invention is directed to a kit having a first material, a second material, and color change agent wherein when at least the first material and the second material are mixed together a bone cement is generated, The kit optionally also contains a color chart including at least one colored area, wherein the colored area contains a reference color for determining whether the bone cement has achieved a given material property after the first material and second material are mixed, Optionally, the kit also contains written instructions instructing a user how to determine when the bone cement has attained a given material property. In one embodiment the material property may be a predefined viscosity state of the bone cement, or alternatively, a predefined temperature threshold, In an embodiment the first material is a powder and the second material is a liquid.

In an alternative embodiment, the instant invention relates to a kit for repairing bone having a first material and a second material, a mixer for mixing at least the first material and the second material to form a bone cement; and a color change agent that provides an indication of a material property of the bone cement during mixing or after mixing the first material and the second material in the mixer. In an embodiment, the color change agent provides a visual or optical indication when the property of the bone cement has reached a material characteristic threshold. In an embodiment, the material characteristic threshold is a predefined viscosity or alternatively, a predefined temperature threshold. The kit of the present invention further optionally may contain written instructions associated with the system. The written instructions can instruct a user to monitor a change in color of the bone cement during mixing or after mixing the first material and the second material.

EXAMPLE

In order to determine the desired processing time and/or application time for the composition containing the bone cement, the exothermic value of the bone cement can be used as an indicator.

During the polymerization of the bone cement, a lot of heat is released and the viscosity increases. By adding a temperature indicator in the form of liquid crystals and/or microencapsulated pigments, a change in color can indicate the suitable temperature and/or viscosity range to apply the cement.

As an example, the following composition is mixed together:

| | |
|---|---|
| powder | 10 g PMMA MW 422 with 2.2% BPO (benzoyl peroxide) (50%) + 3 g BaSO$_4$ + 0.3 g color indicator blue |
| liquid | 4.5 g MMA (methyl methacrylate) + 0.3% DMpT (Di-methyl para toluidine) |

The application time at 21.5° C. in the bone filling device is reached after 8 minutes. At this time, the blue dye in the polymer paste, which remains in the syringe, changes and becomes colorless and indicates that the cement has reached the correct application window. The cement can be released from the bone filling device to the area where the cement is to be applied. The polymer in the syringe turns completely colorless and returns to a blue color after cooling off.

The above description of the embodiments of the invention are not to limit the scope or spirit of the invention. In addition, where methods and steps described above indicate certain events occurring in a certain order, those of ordinary skill in the art will recognize that the ordering of certain steps may be modified and that such modification is in accordance with the invention. Additionally, certain of the steps may be performed concurrently in a parallel process when possible, as well as performed sequentially as described above. Those of ordinary skill in the art will note that modifications can be made to the instant invention without changing the scope of spirit of the invention. Moreover, it is contemplated and therefore within the scope of the present invention that any disclosed one or more element above can be combined with any other one or more elements disclosed above. Ranges of components are discussed above. It is contemplated and therefore within the scope of the present invention that any time a range is given, any number (i.e., any real number) that falls within this range is a contemplated endpoint of that range. For example, if a range of 0.2 to 0.4 is given, any real number that falls within this range, such as 0.3542 is a contemplated endpoint for this range, even if that endpoint is not explicitly mentioned. The present invention is not to be limited by the above description but is rather to be defined by the following claims.

I claim:

1. A method of preparing a bone cement comprising:
   mixing together a powder and a liquid phase to generate a bone cement, wherein the bone cement further includes a thermosensitive color change agent; and
   monitoring the color of the bone cement to determine when to place the bone cement inside a patient's body.

2. The method according to claim 1, wherein the thermosensitive color change agent is added in an amount such that a color threshold is achieved when the bone cement viscosity reaches a predefined viscosity threshold level.

3. The method according to claim 1 further comprising:
   mixing the color change agent with the powder and the liquid phase.

4. The method according to claim 1, wherein either or both of the powder and the liquid phase contain a color change agent.

5. The method of claim 1, wherein either or both of the powder or the liquid phase contain one or more members selected from the group consisting of gentamicin sulfate, erythromycin, tobramycin, vancomycin, cefazolin, oxacillin, cefotaxime, colistin, clindamycin, fusidic acid, barium sulfate, zirconium(IV) oxide, methotrexate, cisplatin, carbon, graphite, aramid, bone particle, polyethylene, titanium, ultra high weight polyethylene, polymethylmethacrylate fibers in a cement matrix, tricalcium phosphate, and hydroxycarbonate apatite.

6. A kit comprising:
   a first material and a second material, wherein when at least the first material and the second material are mixed together a bone cement is generated and wherein the first material, second material, or combination thereof contains a thermosensitive color change agent added in an amount to provide indication on a material property of the bone cement during mixing or after mixing the first material and the second material; and
   a color chart including at least one colored area, wherein the colored area contains a reference color for determining whether the bone cement has achieved the material property after mixing.

7. The kit according to claim 6, wherein the material property is a predefined viscosity state of the bone cement.

8. The kit according to claim 6, wherein the material property is a predefined temperature threshold.

9. The kit according to claim 6, wherein the first material is a powder and a second material is a liquid.

10. The kit according to claim 6, further comprising written instructions which instruct a user to monitor a change in color of the bone cement during mixing or after mixing the first material and the second material.

11. A kit for repairing bone comprising:
    a first material and a second material; a mixer for mixing at least the first material and the second material to form a bone cement;
    a thermosensitive color change agent contained within the first material, the second material, or a combination thereof, wherein the thermosensitive color change agent is added in an amount to provide an indication on a material property of the bone cement during mixing or after mixing the first material and the second material in the mixer; and
    written instructions which instruct a user to monitor a change in color of the bone cement during mixing or after mixing the first material and the second material.

12. The kit according to claim 11, wherein the material characteristic threshold is a predefined viscosity.

* * * * *